(12) United States Patent
Hirama et al.

(10) Patent No.: US 10,513,565 B2
(45) Date of Patent: *Dec. 24, 2019

(54) LOW-SUBSTITUTED HYDROXYPROPYL CELLULOSE, PRODUCTION METHOD THEREOF, AND SOLID PREPARATION

(71) Applicant: SHIN-ETSU CHEMICAL CO., LTD., Tokyo (JP)

(72) Inventors: Yasuyuki Hirama, Joetsu (JP); Aya Tsuchiya, Yokohama (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/722,594

(22) Filed: Oct. 2, 2017

(65) Prior Publication Data

US 2018/0100027 A1 Apr. 12, 2018

(30) Foreign Application Priority Data

Oct. 7, 2016 (JP) ................... 2016-199097

(51) Int. Cl.
| | |
|---|---|
| *C08B 11/08* | (2006.01) |
| *A61K 9/20* | (2006.01) |
| *A61K 47/38* | (2006.01) |
| *C08B 3/08* | (2006.01) |
| *C08B 3/14* | (2006.01) |
| *C08B 11/193* | (2006.01) |
| *G01N 23/20* | (2018.01) |
| *A61K 9/14* | (2006.01) |
| *C09D 101/30* | (2006.01) |
| *C08L 1/32* | (2006.01) |

(52) U.S. Cl.
CPC .............. *C08B 3/08* (2013.01); *A61K 9/2054* (2013.01); *C08B 3/14* (2013.01); *C08B 11/08* (2013.01); *C08B 11/193* (2013.01); *A61K 9/146* (2013.01); *A61K 47/38* (2013.01); *C08L 1/32* (2013.01); *C09D 101/30* (2013.01); *G01N 23/20* (2013.01)

(58) Field of Classification Search
CPC ........ C08B 11/08; A61K 9/2054; A61K 47/38
See application file for complete search history.

(56) References Cited

U.S. PATENT DOCUMENTS

| 4,091,205 A | 5/1978 | Onda et al. |
|---|---|---|
| 2003/0166918 A1 | 9/2003 | Obara |
| 2008/0038339 A1 | 2/2008 | Hoshino et al. |
| 2008/0039621 A1 | 2/2008 | Maruyama et al. |
| 2015/0299338 A1 | 10/2015 | Yoshida |

FOREIGN PATENT DOCUMENTS

| EP | 1342733 A1 | 9/2003 |
|---|---|---|
| EP | 2366720 A1 | 9/2011 |
| EP | 2659880 A1 | 11/2013 |
| EP | 2937363 A1 | 10/2015 |
| GB | 482885 A | 4/1938 |
| JP | S51-063927 A | 6/1976 |
| JP | 2008-133432 A | 6/2008 |

OTHER PUBLICATIONS

Mar. 21, 2018 Extended European Search Report issued in Patent Application No. 17195313.6.
Mar. 21, 2018 Extended European Search Report issued in Patent Application No. 17195312.8.
Brännvall, Elisabet et al., "Pulp Characterisation.", Pulping Chemistry and Techno, De Gruyter, pp. 429-459, year: 2009.
U.S. Appl. No. 15/722,588, filed Oct. 2, 2017 in the name of Hirama.

*Primary Examiner* — Jonathan S Lau
(74) *Attorney, Agent, or Firm* — Oliff PLC (57) ABSTRACT

Provided are low-substituted hydroxypropyl cellulose (L-HPC) having a hydroxypropoxy content of from 5 to 16% by weight, and having, on a basis of a dynamic image analysis to divide all particles into fine, spherical, and fibrous particles consisting of long and short fibrous particles, a volume fraction of the long fibrous particles of from 15 to 50% and a volume fraction of the short fibrous particles of from 23 to 60%; and a solid preparation containing the L-HPC. Also provided is a method for producing the L-HPC including the steps: bringing sheet-like or chip-like pulp having a length-weighted average fiber length of from 2.40 to 3.50 mm into contact with an alkali metal hydroxide solution, reacting the resulting alkali cellulose with propylene oxide, and dispersing the resulting reaction product in water containing an acid to partially dissolve it therein, followed by neutralization with an acid to precipitate crude L-HPC.

8 Claims, 1 Drawing Sheet

LOW-SUBSTITUTED HYDROXYPROPYL CELLULOSE, PRODUCTION METHOD THEREOF, AND SOLID PREPARATION

BACKGROUND OF THE INVENTION

1. Field of the Invention

The invention relates to low-substituted hydroxypropyl cellulose to be added as a disintegrant or a binder to a solid preparation in the fields of pharmaceuticals or food, the low-substituted hydroxypropyl cellulose having good compressibility and capping-prevention performance.

2. Related Art

A solid preparation as a pharmaceutical product, healthy food or the like disintegrates since a disintegrant contained therein absorbs water and swells therein. Examples of the disintegrant include low-substituted hydroxypropyl cellulose, carboxymethyl cellulose and a calcium salt thereof, and starch and a derivative thereof.

Particularly in the field of pharmaceuticals, the number of newly developed drugs which lack stability is increasing and an additive therefor has been limited from the standpoint of their mutual action. Under the circumstances, the low-substituted hydroxypropyl cellulose has been used widely as a nonionic disintegrant or binder and can be regarded as a preferable additive.

A tablet, which is one of the dosage forms of the solid preparation as a pharmaceutical product or food, is a solid preparation obtained by compressing powder into a predetermined shape. The tablet has advantages such as handling ease. Particularly in the fields of pharmaceuticals, a production amount of the tablet is about 50% of the total production amount of pharmaceuticals. Thus, the tablet is the most popular dosage form.

The tablet can be produced by, for example, a dry direct tableting method, a dry granulation tableting method, an extrusion granulation tableting method, or a wet granulation tableting method. The dry direct tableting method is a method of directly tableting a mixture of a drug, an excipient and the like into a tablet. The dry direct tableting method is more advantageous than the wet granulation tableting method because the dry direct tableting method can omit granulation, drying and sizing steps, thereby making the process simple and the production cost reduced greatly. On the other hand, the dry direct tableting method is more likely to cause problems such as uneven drug contents, variation in tablet weight, and a tableting trouble, compared with the wet granulation tableting method. The tableting trouble mean a trouble happening during tableting and typical examples of the tableting trouble include sticking, binding, and capping. In particular, the capping is a tableting trouble in which a portion of a tablet separates to form a cap. The capping results in not only an unusual appearance but also reduction of the drug content so that the capping should be prevented.

There is known a method of controlling the amount of particles in fibrous form by dispersing the etherification reaction product in water containing an acid in such an amount as to be from 5 to 80% of the amount required for neutralizing the total amount of alkali to dissolve a portion of low-substituted hydroxypropyl cellulose therein (JP 51-063927A). The low-substituted hydroxypropyl cellulose produced by the above method has good compressibility due to entanglement among fibrous particles so that the capping can be prevented during the dry direct tableting or wet granulation tableting method.

There is also known a method of decreasing the amount of particles in fibrous form by neutralizing all the alkali present in the etherification reaction product without dissolving a portion of the low-substituted hydroxypropyl cellulose, and subjecting to compaction-grinding (JP 2008-133432A). The low-substituted hydroxypropyl cellulose obtained by this method has good flowability and has compressibility better than that of the low-substituted hydroxypropyl cellulose of JP 51-063927A in spite of the absence of the particles in fibrous form.

SUMMARY OF THE INVENTION

However, when the low-substituted hydroxypropyl cellulose described in JP 51-063927A or JP 2008-133432A is used for the dry direct tableting or the like, the capping may occur due to insufficient compressibility. Thus, there is a demand for further improvement in compressibility.

The invention has been made to overcome the drawback of the above-described prior art. An object of the invention is to provide low-substituted hydroxypropyl cellulose having good compressibility and capping-prevention performance.

As a result of an extensive investigation with a view to achieving the object, the inventors have found that low-substituted hydroxypropyl cellulose having respective portions of long fibrous particles and short fibrous particles controlled shows good compressibility and capping-prevention performance, and have completed the invention.

In one aspect of the invention, there is provided low-substituted hydroxypropyl cellulose having a hydroxypropoxy content of from 5 to 16% by weight, and having, on a basis of a dynamic image analysis to divide all particles into fine particles, spherical particles, and fibrous particles consisting of long and short fibrous particles, a volume fraction of the long fibrous particles relative to all of the particles of from 15 to 50% and a volume fraction of the short fibrous particles relative to all of the particles of from 23 to 60%, wherein the fine particles have a length of fiber of less than 40 µm, the spherical particles have a length of fiber of 40 µm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a maximal Feret diameter to a minimal Feret diameter, of 0.5 or more, and a circularity, which is a ratio of a perimeter ($P_{EQPC}$) of a circle that has the same area as a projection area to a perimeter ($P_{real}$) of a real particle, of 0.7 or more, the long fibrous particles have a length of fiber of 200 µm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7, and the short fibrous particles have a length of fiber of 40 µm or more and less than 200 µm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7.

In another aspect of the invention, there is also provided a solid preparation comprising the low-substituted hydroxypropyl cellulose.

In a further aspect of the invention, there is provided a method for producing the low-substituted hydroxypropyl cellulose comprising the steps of: bringing sheet-like pulp or chip-like pulp having a length-weighted mean length of from 2.40 to 3.50 mm into contact with an alkali metal hydroxide solution to obtain alkali cellulose; reacting the alkali cellulose with propylene oxide to obtain a reaction product; dispersing the reaction product in water comprising an acid to partially dissolve the reaction product therein, followed by neutralization with an acid to precipitate crude low-substituted hydroxypropyl cellulose; washing the crude low-substituted hydroxypropyl cellulose to obtain washed low-substituted hydroxypropyl cellulose; drying the washed low-substituted hydroxypropyl cellulose to obtain dried low-substituted hydroxypropyl cellulose; and pulverizing the dried low-substituted hydroxypropyl cellulose.

According to the invention, since the low-substituted hydroxypropyl cellulose has good compressibility and capping-prevention performance, a high-quality solid preparation can be produced. For example, a high-quality tablet causing less capping during tableting, coating, filling, transporting or the like can be produced. In addition, high-quality granules or the like causing less cracks during filling, transporting or the like can be produced.

DETAILED DESCRIPTION OF THE PREFERRED EMBODIMENTS

Figure 1:
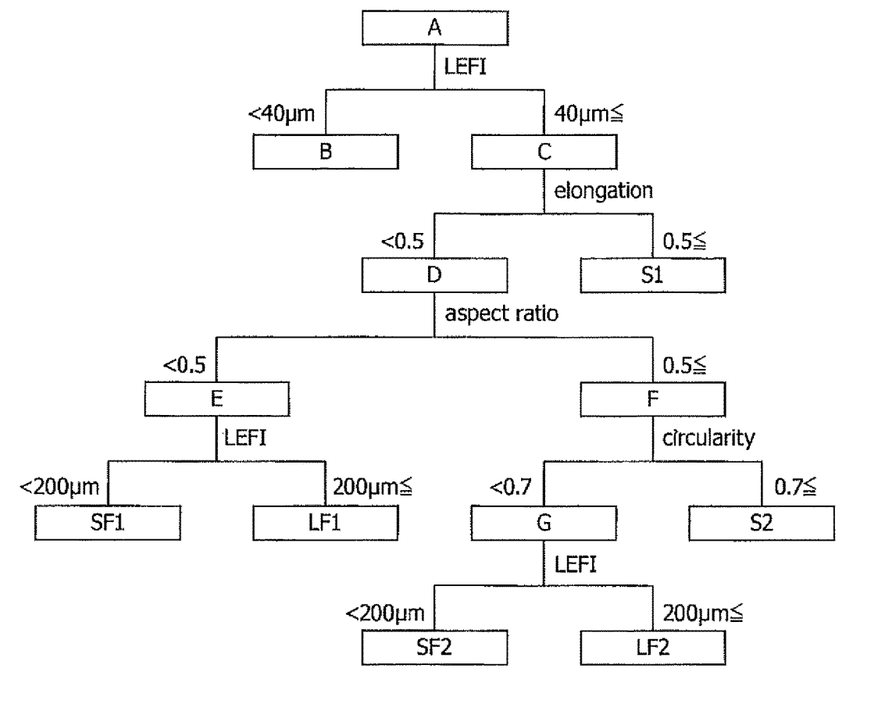
FIG. 1 is a flowchart of dividing the "all particles" of low-substituted hydroxypropyl cellulose into four types of particles, "fine particles", "long fibrous particles (LF1 and LF2)", "short fibrous particles (SF1 and SF2)", and "spherical particles (S1 and S2)".

In the specification, low-substituted hydroxypropyl cellulose is divided into four types of particles, "long fibrous particles", "short fibrous particles", "spherical particles", and "fine particles". FIG. 1 is a flowchart that summarizes the division of "all particles" of a hydroxyalkyl alkyl cellulose into four types of particles, "fine particles", "long fibrous particles (LF1 and LF2)", "short fibrous particles (SF1 and SF2)", and "spherical particles (S1 and S2)".

Each volume fraction of the respective types of particles of low-substituted hydroxypropyl cellulose can be determined by measuring shape parameters including a length of fiber (LEFI), a diameter of fiber (DIFI), an elongation, an aspect ratio, and a circularity, by the dynamic image analysis. The dynamic image analysis is a method in which images of particles dispersed in a fluid such as a gas and a solvent are continuously recorded and are binarized and analyzed to obtain a particle diameter or a particle shape. The analysis can be performed by using, for example, a dynamic image analysis type particle diameter distribution analyzer, QICPIC/R16 (manufactured by Sympatec GmbH).

All particles A are divided into particles C having a length of fiber (LEFI) of 40 µm or more and fine particles B having a length of fiber of less than 40 µm. The LEFI is defined as the length of the longest direct path that connects the ends of the particle within the contour of the particle. A QICPIC/R16 equipped with an M7 lens has a detection limit of 4.7 µm and thus fails to detect a particle having an LEFI of less than 4.7 µm. However, the volume of particles having an LEFI of less than 4.7 µm is extremely small relative to that of all particles of the low-substituted hydroxypropyl cellulose so that it is negligible for the purpose of the invention.

The particles C having an LEFI of 40 µm or more are divided into first spherical particles (S1) having an elongation of 0.5 or more and particles D having an elongation of less than 0.5, wherein the elongation is a ratio of a diameter of fiber (DIFI) to LEFI (DIFI/LEFI) of the particle. The DIFI is defined as the minor diameter of a particle, and is calculated by dividing the projection area of the particle by the sum of all lengths of the fiber branches of the particle.

The particles D having an LEFI of 40 µm or more and an elongation of less than 0.5 are divided into particles E having an aspect ratio of less than 0.5 and particles F having an aspect ratio of 0.5 or more, wherein the aspect ratio is a ratio ($F_{min}/F_{max}$) of minimal Feret diameter ($F_{min}$) to maximal Feret diameter ($F_{max}$). Each particle has an aspect ratio of more than 0 and not more than 1. The Feret diameter is the distance between two parallel tangent lines that put the particle therebetween. The maximal Feret diameter ($F_{max}$) is the largest distance between pairs of tangent lines to the particle in consideration of all possible orientations by changing the directions from 0° to 180°, and the minimal Feret diameter ($F_{min}$) is a minimal distance between pairs of tangent lines to the particle in consideration of all possible orientations by changing the directions from 0° to 180°.

The fibrous particles E having an LEFI of 40 µm or more, an elongation of less than 0.5, and an aspect ratio of less than 0.5 are divided into first long fibrous particles (LF1) having an LEFI of 200 µm or more and first short fibrous particles (SF1) having an LEFI of less than 200 µm.

The particles F having an LEFI of 40 µm or more, an elongation of less than 0.5, and an aspect ratio of 0.5 or more are divided into second spherical particles (S2) having a circularity of 0.7 or more and fibrous particles G having a circularity of less than 0.7. The circularity is a ratio of the perimeter ($P_{EQPC}$) of a circle that has the same area as the projection area ($A_p$) of the particle to the perimeter ($P_{real}$) of the real particle, and is defined by the following equation. Each particle has a circularity of more than 0 and not more than 1. A particle having a smaller circularity has a more irregular shape. The EQPC is the diameter of a circle of an equal projection area, and is defined as the diameter of a circle that has the same area as the projection area of the particle, and is also called Heywood diameter.

$$\text{Circularity} = P_{EQPC}/P_{real} = 2\sqrt{\pi \cdot A_p}/P_{real}$$

The fibrous particles G having an LEFI of 40 µm or more, an elongation of less than 0.5, an aspect ratio of 0.5 or more, and a circularity of less than 0.7 are divided into second long fibrous particles (LF2) having an LEFI of 200 µm or more and second short fibrous particles (SF2) having an LEFI of less than 200 µm.

The volume ($V_m$) of the fine particles of low-substituted hydroxypropyl cellulose can be calculated by the following equation where each fine particle is assumed to be a sphere having a diameter of EQPC.

$$V_m = (\pi/6) \times (EQPC)^3 \times N_m,$$

wherein $N_m$ is the number of fine particles in a sample, and EQPC is a median EQPC corresponding to the 50% cumulative value on a number-based cumulative particle diameter distribution curve of the fine particles.

In the specification, particles having an LEFI of 40 µm or more, which are particles other than the fine particles having an LEFI of less than 40 µm among the all particles, are divided, on the basis of such above shape parameters of particles as LEFI, an elongation, an aspect ratio, and a circularity, into "long fibrous particles", "short fibrous particles", and "spherical particles", which are distinguished from each other.

<Long Fibrous Particles>

Particles satisfying the following definition of LF1 or LF2 are combined into "long fibrous particles".

LF1: particles having an elongation of less than 0.5, an aspect ratio of less than 0.5, and an LEFI (length of fiber) of 200 μm or more, and LF2: particles having an elongation of less than 0.5, an aspect ratio of 0.5 or more, a circularity of less than 0.7, and an LEFI (length of fiber) of 200 μm or more.

The volume ($V_{LF}$) of the long fibrous particles of low-substituted hydroxypropyl cellulose can be calculated by the following equation wherein each long fibrous particle is assumed to be a cylindrical column having a DIFI as a bottom diameter and an LEFI as a height.

$$V_{LF}=(\pi/4)\times(DIFI)^2\times(LEFI)\times N_{LF},$$

wherein $N_{LF}$ is the number of long fibrous particles in the sample, DIFI is a median DIFI corresponding to the 50% cumulative value on a number-based cumulative particle diameter distribution curve of the long fibrous particles, and LEFI is a median LEFI corresponding to the 50% cumulative value on a number-based cumulative particle diameter distribution curve of the long fibrous particles.

The volume of particles satisfying the definition LF1 and the volume of particles satisfying the definition LF2 are calculated in accordance with the above equation, respectively, and a sum of the volumes means the volume of the long fibrous particles of a hydroxyalkyl alkyl cellulose.

<Short fibrous particles>

Particles satisfying the following definition of SF1 or SF2 are combined into "short fibrous particles".

SF1: particles having an elongation of less than 0.5, an aspect ratio of less than 0.5, and an LEFI (length of fiber) of not less than 40 μm and less than 200 μm, and SF2: particles having an elongation of less than 0.5, an aspect ratio of 0.5 or more, a circularity of less than 0.7, and an LEFI (length of fiber) of not less than 40 μm and less than 200 μm.

The volume ($V_{SF}$) of the short fibrous particles of low-substituted hydroxypropyl cellulose can be calculated by the following equation where each short fibrous particle is assumed to be a cylindrical column having a bottom diameter of DIFI and a height of LEFI, in the same manner as for the above long fibrous particles.

$$V_{SF}=(\pi/4)\times(DIFI)^2\times(LEFI)\times N_{SF},$$

wherein $N_{SF}$ is the number of short fibrous particles in the sample, DIFI is a median DIFI corresponding to the 50% cumulative value on a number-based cumulative particle diameter distribution curve of the short fibrous particles, and LEFI is a median LEFI corresponding to the 50% cumulative value on a number-based cumulative particle diameter distribution curve of the short fibrous particles.

The volume of particles satisfying the definition of SF1 and the volume of particles satisfying the definition of SF2 are calculated in accordance with the above equation, respectively, and a sum of the volumes means the volume of the short fibrous particles of low-substituted hydroxypropyl cellulose.

<Spherical Particles>

Particles satisfying the definition of S1 or S2 are combined into "spherical particles".

S1: particles having an LEFI (length of fiber) of 40 μm or more, and an elongation of 0.5 or more, and S2: particles having an LEFI (length of fiber) of 40 μm or more, an elongation of less than 0.5, an aspect ratio of 0.5 or more, and a circularity of 0.7 or more.

The volume ($V_S$) of the spherical particles of low-substituted hydroxypropyl cellulose can be calculated by the following equation where each spherical particle is assume to be a sphere having a diameter of EQPC.

$$V_S=(\pi/6)\times(EQPC)^3\times N_S,$$

wherein $N_S$ is the number of spherical particles in the sample, and EQPC is a median EQPC corresponding to the 50% cumulative value on a number-based particle diameter cumulative distribution curve of the spherical particles.

The volume of particles satisfying the definition S1 and the volume of particles satisfying the definition S2 are calculated in accordance with the above equation, respectively, and a sum of the volumes means the volume of the spherical particles of low-substituted hydroxypropyl cellulose.

The volume fraction of each type of particles of low-substituted hydroxypropyl cellulose can be calculated from the following corresponding equation on a basis of the above-defined volumes, $V_m$, $V_{LF}$, $V_{SF}$, and $V_S$.

$$\text{Volume fraction of fine particles}=\{V_m/(V_m+V_{LF}+V_{SF}+V_S)\}\times 100$$

$$\text{Volume fraction of long fibrous particles}=\{V_{LF}/(V_m+V_{LF}+V_{SF}+V_S)\}\times 100$$

$$\text{Volume fraction of short fibrous particles}=\{V_{SF}/(V_m+V_{LF}+V_{SF}+V_S)\}\times 100$$

$$\text{Volume fraction of spherical particles}=\{V_S/(V_m+V_{LF}+V_{SF}+V_S)\}\times 100$$

The low-substituted hydroxypropyl cellulose has a volume fraction of long fibrous particles of from 15 to 50%, preferably from 18 to 48%, more preferably from 20 to 46% from the standpoint of good flowability, high compressibility, and capping-prevention performance.

The low-substituted hydroxypropyl cellulose has a volume fraction of short fibrous particles of from 23 to 60%, preferably from 25 to 50%, more preferably from 25 to 40% from the standpoint of good flowability, high compressibility, and capping-prevention performance.

The low-substituted hydroxypropyl cellulose has a ratio of the volume fraction of short fibrous particles to the volume fraction of long fibrous particles (short fibrous particles/long fibrous particles) of preferably from 0.50 to 1.50, more preferably from 0.60 to 1.40, still more preferably from 0.70 to 1.30, from the standpoint of good flowability, high compressibility, and capping-prevention performance.

The low-substituted hydroxypropyl cellulose has a volume fraction of fibrous particles, in other words, a total volume fraction of long and short fibrous particles of preferably from 45 to 80%, more preferably from 50 to 70%, still more preferably from 50 to 65%, from the standpoint of good flowability, high compressibility, and capping-prevention performance.

The low-substituted hydroxypropyl cellulose has a volume fraction of spherical particles of preferably from 18 to 50%, more preferably from 20 to 45%, still more preferably from 25 to 40%, from the standpoint of good flowability, high compressibility, and capping-prevention performance.

The low-substituted hydroxypropyl cellulose has a volume fraction of fine particles of preferably less than 10.0%, more preferably less than 8.0%, still more preferably less than 5.0%, from the standpoint of good flowability.

The low-substituted hydroxypropyl cellulose has a hydroxypropoxy content of from 5 to 16% by weight, preferably from 6 to 15% by weight, more preferably from 7 to 14% by weight. Low-substituted hydroxypropyl cellulose having a hydroxypropoxy content of less than 5% by weight has low swelling by water absorption. Low-substituted hydroxypropyl cellulose having a hydroxypropoxy content of more than 16% by weight has an increased water solubility so that a solid preparation comprising it has insufficient disintegrability. The hydroxypropoxy content can be determined by the assay described in the "low-substituted hydroxypropyl cellulose" of the Japanese Pharmacopoeia Seventeenth Edition.

The low-substituted hydroxypropyl cellulose has a volume-based average particle diameter, determined by a dry laser diffractometry, of preferably from 10 to 120 μm, more preferably from 30 to 100 μm, still more preferably from 40 to 90 μm, particularly preferably from 50 to 70 μm, from the standpoint of disintegrability and compressibility. The volume-based average particle diameter means a diameter corresponding to the 50% cumulative value of a volume-based cumulative particle diameter distribution curve, and it may be measured using, for example, a laser diffraction particle diameter distribution analyzer "Mastersizer 3000" (produced by Malvern Instruments Ltd).

The low-substituted hydroxypropyl cellulose may be used as a binder or disintegrant of a solid preparation such as a tablet, a granule, a fine granule or a capsule. The low-substituted hydroxypropyl cellulose is particularly suited as a tablet, which is easy to handle and most popularly used. The tablet may be obtained by any one of the dry direct tableting method, the wet mixing granulation tableting method, the fluidized-bed granulation tableting method, and the dry granulation tableting method. The dry direct tableting method is particularly suited because its production process is simple and contains production steps more simplified than those of the wet mixing granulation tableting method and others, thereby greatly reducing a production cost.

The term "granule" or "fine granule" means a product obtained by granulating a mixture containing at least the low-substituted hydroxypropyl cellulose and a drug. The capsule may be produced by encapsulating the granules or fine granules.

The low-substituted hydroxypropyl cellulose content in the solid preparation is preferably from 2 to 50% by weight, more preferably from 5 to 30% by weight, still more preferably from 5 to 20% by weight, from the standpoint of compressibility, disintegrability and storage stability.

A method for producing a tablet comprising the low-substituted hydroxypropyl cellulose by the dry direct tableting will next be described. In the dry direct tableting, a tablet may be produced by a method comprising a step of compressing a mixture of at least the low-substituted hydroxypropyl cellulose, a drug and a lubricant with a tableting machine at a predetermined pressure. The drug may be in any one of the following forms: fine powder, crude particles, and a granulated product. The lubricant is used in an amount of preferably from 0.05 to 2.0 parts by weight relative to 100 parts by weight of the mixture containing at least the low-substituted hydroxypropyl cellulose and the drug (excluding the lubricant).

A tablet may be produced by using a tableting machine such as a rotary tableting machine or a single-punch tableting machine. The size of the tablet may be selected freely. A tablet diameter is preferably from 6 to 12 mm from the standpoint of handling ease and ingestability, and a tablet weight (i.e. weight per tablet) is preferably from 70 to 700 mg The tableting pressure during tableting is preferably from 50 to 300 MPa from the standpoint of tablet hardness and reduction of tableting troubles.

The capping incidence of tablets is preferably 0% from the standpoint of the quality of the tablets. The capping incidence can be determined by the method comprising the steps of: turning a drum having 50 tablets therein 100 times for 4 minutes at 25 rpm, and counting the number of tablets which have caused capping by using a tablet friability tester described in "Tablet Friability Test" of the Japanese Pharmacopoeia Seventeenth Edition. For example, it can be measured using a friability tester TA (product of ERWEKA GmbH).

The low-substituted hydroxypropyl cellulose has compressibility of preferably 150N or more, more preferably 180N or more, from the standpoint of tablet hardness or reduction of capping incidence.

The compatibility of the low-substituted hydroxypropyl cellulose means the hardness of a tablet obtained by compressing 450 mg of the low-substituted hydroxypropyl cellulose having such a controlled humidity as to have a loss on drying (i.e. water content) of from 2.8 to 3.8% by weight, with a single-punch tableting machine using a round flat type punch having a diameter of 12 mm at a tableting pressure of 10.0 kN (about 88.5 MPa).

The loss on drying (i.e. water content) can be determined by the method described in "Loss on Drying test" in "General Tests" of the Japanese Pharmacopoeia Seventeenth Edition.

The hardness of the tablet can be measured from the maximum strength at break at which the tablet is broken by a load applied at a predetermined rate in the diameter direction of the tablet. For example, it can be measured using a tablet hardness tester "TBH-125" (product of ERWEKA GmbH).

The drug to be used for producing a solid preparation comprising the low-substituted hydroxypropyl cellulose in accordance with the invention is not particularly limited insofar as it is orally administrable. Examples of the drug include a central nervous system drug, a circulatory system drug, a respiratory system drug, a digestive system drug, an antibiotic, an antitussive and expectorant drug, an antihistamine drug, an antipyretic, analgesic and anti-inflammatory drug, a diuretic drug, an autonomic drug, an antimalarial drug, an anti-diarrheal drug, a psychotropic drug, and vitamins and derivatives thereof.

Examples of the central nervous system drug include diazepam, idebenone, paracetamol, naproxen, piroxicam, indomethacin, sulindac, lorazepam, nitrazepam, phenytoin, acetaminophen, ethenzamide, and chlordiazepoxide.

Examples of the circulatory system drug include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, and alprenolol hydrochloride.

Examples of the respiratory system drug include amlexanox, dextromethorphan, theophylline, pseudoephedrine, salbutamol, and guaifenesin.

Examples of the digestive system drug include a benzimidazole-based drug having an anti-ulcer action such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicyclic acid.

Examples of the antibiotic include talampicillin hydrochloride, bacampicillin hydrochloride, cefaclor, and erythromycin.

Examples of the antitussive and expectorant drug include noscapine hydrochloride, carbetapentane citrate, isoaminile citrate, and dimemorfan phosphate.

Examples of the antihistamine drug include chlorpheniramine maleate, diphenhydramine hydrochloride, and promethazine hydrochloride.

Examples of the antipyretic, analgesic and anti-inflammatory drug include ibuprofen, diclofenac sodium, flufenamic acid, sulpyrine, aspirin, and ketoprofen.

Examples of the diuretic drug include caffeine.

Examples of the autonomic drug include dihydrocodeine phosphate, dl-methylephedrine hydrochloride, atropine sulfate, acetylcholine chloride, and neostigmine.

Examples of the antimalarial drug include quinine hydrochloride.

Examples of the anti-diarrheal drug include loperamide hydrochloride.

Examples of the psychotropic drug include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate, and tranexamic acid.

In the production of the solid preparation containing the low-substituted hydroxypropyl cellulose, a disintegrant, a binder, an extender, a taste corrigent component, a flavor, a lubricant, and/or the like used commonly for a solid preparation may be used in a typical amount.

Examples of the disintegrant include corn starch, potato starch, partly pregelatinized starch, carboxymethyl starch sodium, carmellose, croscarmellose sodium, crystalline cellulose, and crospovidone.

Examples of the binder include hydroxypropyl cellulose, polyvinylpyrrolidone, and hydroxypropylmethyl cellulose.

Examples of the extender include erythritol, mannitol, sorbitol, lactose, sucrose, calcium phosphate, and calcium sulfate.

Examples of the taste corrigent component include citric acid, tartaric acid, and malic acid.

Examples of the flavor include menthol, peppermint oil, and vanillin.

Examples of the lubricant include magnesium stearate and sucrose fatty acid ester.

Next, a method for producing low-substituted hydroxypropyl cellulose will be described.

Pulp has a length-weighted mean length of from 2.40 to 3.50 mm, preferably from 2.60 to 3.30 mm, more preferably from 2.70 to 3.10 mm, from the standpoint of the volume fraction of long fibrous particles and flowability. The pulp having a length-weighted mean length of 2.40 mm or more is inferior in absorption of an alkali so that it is difficult to obtain uniform alkali cellulose. Thus, the pulp having a length-weighted mean length of 2.40 mm or more has not been used conventionally for producing even low-substituted hydroxypropyl cellulose having a low degree of hydroxypropoxy substitution, until the present invention.

The pulp has a length-weighted mean width of preferably more than 25 μm and 32 μm or less, more preferably from 27 to 30 μm from the standpoint of the volume fraction of long fibrous particles and flowability.

As the pulp, sheet-like pulp or chip-like pulp may be used from the standpoint of the length-weighted mean length.

The length-weighted mean length and length-weighted mean width of the pulp may be determined in accordance with the method (automated optical analysis) of JIS (Japanese Industrial Standards) P 8226. They can be measured using, for example, a Kajaani fiber length analyzer FS300 (product of Metso Automation).

As the pulp, wood pulp or cotton linter pulp may be used. The wood-derived pulp is particularly preferred from the standpoint of the absence of GMO-free (GMO: genetically modified organism). As the wood species, a needle-leaved tree such as pine, spruce or hemlock, or a broad-leaved tree such as eucalyptus or maple may be used.

The method for producing the low-substituted hydroxypropyl cellulose comprises the steps of: bringing pulp having a length-weighted mean length of from 2.40 to 3.50 mm into contact with an alkali metal hydroxide solution to obtain alkali cellulose; reacting the alkali cellulose with propylene oxide to obtain a reaction product; dispersing the reaction product in water comprising an acid to partially dissolve the reaction product therein, followed by neutralization with an acid to precipitate crude low-substituted hydroxypropyl cellulose; washing the crude low-substituted hydroxypropyl cellulose to obtain washed low-substituted hydroxypropyl cellulose; drying the washed low-substituted hydroxypropyl cellulose to obtain dried low-substituted hydroxypropyl cellulose; and pulverizing the dried low-substituted hydroxypropyl cellulose.

More specifically, first, starting material sheet-like or chip-like pulp is brought into contact with an alkali metal hydroxide solution such as an aqueous sodium hydroxide solution to obtain alkali cellulose. The alkali cellulose can be obtained, for example, by immersing sheet-like or chip-like pulp in the aqueous sodium hydroxide solution and then pressing the resulting pulp. Next, the alkali cellulose is reacted with propylene oxide. The reaction may be carried out in the internal stirring type reactor following the production of the alkali cellulose, or the reaction may be carried out in another reactor into which the alkali cellulose produced has been introduced.

Then, the reaction product thus obtained is dispersed in water comprising an acid such as acetic acid or hydrochloric acid to dissolve a portion of the low-substituted hydroxypropyl cellulose therein. The amount of the acid is preferably from 5 to 80%, more preferably from 10 to 60%, still more preferably from 10 to 40% of an amount (equivalent amount) required for neutralizing the alkali metal hydroxide present in the reaction product. An acid such as acetic acid or hydrochloric acid is added further to completely neutralize the remaining alkali metal hydroxide, thereby precipitating crude low-substituted hydroxypropyl cellulose. The equivalent amount required for neutralizing the alkali metal hydroxide present in the reaction product is an equivalent amount required for neutralizing the alkali metal hydroxide in the alkali metal hydroxide solution used for the contact with the pulp.

Next, the crude low-substituted hydroxypropyl cellulose is purified in the washing step, and then subjected to the drying step and the pulverization step to obtain desired low-substituted hydroxypropyl cellulose.

In the pulverization step, an impact pulverizer is preferably used. Examples of the impact pulverizer may include a hammer mill, an impact mill, and Victory mill. Further, it is preferred to sieve the pulverized low-substituted hydroxypropyl cellulose by a conventional method to remove coarse powder which has been insufficiently pulverized. A sieve having an opening of preferably from 75 to 180 μm may be used.

EXAMPLES

The invention will hereinafter be described specifically by Examples and Comparative Examples. It should not be construed that the invention is limited by or to Examples.
<Pulp Used>

The length-weighted mean length and length-weighted mean width of sheet-like pulp were determined in accordance with the method of JIS P8226, by analyzing 50 mL of a dispersion prepared by sufficiently dispersing the pulp in water, with a Kajaani fiber length analyzer FS300 (product of Metso Automation Inc.).

Sheet-like Pulps A to F were used. A length-weighted mean length and a length-weighted mean width of each of Pulps A to F were respective 2.56 mm and 26 μm for Pulp A, 2.76 mm and 28 μm for Pulp B, 2.95 mm and 29 μm for Pulp C, 2.33 mm and 26 μm for Pulp D, 2.12 mm and 24 μm for Pulp E, and 1.70 mm and 21 μm for Pulp F.

Example 1

Sheet-like Pulp A derived from wood and having a length-weighted mean length of 2.56 mm and a length-weighted mean width of 26 μm was immersed in an aqueous sodium hydroxide solution having a concentration of 43% by weight, and then pressed to obtain alkali cellulose containing 22.0% by weight of sodium hydroxide. A reactor was charged with 100 parts by weight of the resulting alkali cellulose and purged with nitrogen. The reactor was then subjected to addition of 11.3 parts by weight of propylene oxide. The resulting mixture was reacted with stirring at a jacket temperature of 50° C. for 2 hours and then at a jacket temperature of 60° C. for 1 hour to obtain 108.0 parts by weight of reaction product.

A kneader was charged with 250 parts by weight of warm water of 45° C. and 3.3 parts by weight (10% of the neutralization equivalent) of acetic acid. The reaction product was introduced and dispersed therein, and stirred at a jacket temperature of 45° C. for 40 minutes to dissolve a portion of low-substituted hydroxypropyl cellulose. Then 29.7 parts by weight (90% of the neutralization equivalent) of acetic acid were added thereto for complete neutralization to precipitate crude low-substituted hydroxypropyl cellulose. The precipitate was dispersed in 3000 parts by weight of hot water of about 90° C. The dispersion was washed and dehydrated using a batch type centrifugal separator at a rotational speed of 3000 rpm, and then dried in a shelf dryer at 80° C. for 18 hours. The dried product was pulverized by an impact mill ("Victory Mill VP-1", product of Hosokawa Micron), and the pulverized product was sifted through a sieve having an opening of 75 μm to obtain low-substituted hydroxypropyl cellulose.

The hydroxypropoxy content of the low-substituted hydroxypropyl cellulose thus obtained was determined and as described below, the average particle diameter, volume fraction of various particles (long and short fibrous particles, spherical particles, and fine particles), and compressibility were also determined. The results are shown in Table 1.

<Determination of Average Particle Diameter>

The average particle diameter was determined by measuring a diameter corresponding to the 50% cumulative value of a volume-based cumulative particle diameter distribution curve under conditions of a dispersion pressure of 2 bar and scattering intensity of from 2 to 10% by a dry method based on Fraunhofer diffraction theory by using a laser diffraction particle diameter distribution analyzer "Mastersizer 3000" (product of Malvern Instrument Ltd).

<Determination of Volume Fractions of Various Particles>

The volume fraction of each of various particles (long and short fibrous particles, spherical particles, and fine particles) was determined by a method comprising the steps of: subjecting sample particles to the measurement using a dynamic image analysis type particle diameter distribution analyzer "QICPIC/R16" (product of Sympatic GmbH) equipped with a constant feeder "VIBRI/L", an air-flow type disperser "RODOS/L", and an M7 lens under the conditions of a frame rate of 500 Hz, an injector of 4 mm, and a dispersion pressure of 1 bar to obtain images of the particles; analyzing the images of the particles by an analysis software "WINDOX5 Version:5.9.1.1" to find a number-based median EQPC, a number-based median LEFI, a number-based median DIFI, an elongation ratio, an aspect ratio, and a circularity of each of the particles; and calculating the volume fractions based on the values thus found, in accordance with the above-described equations. The division used during the analysis was M7.

<Determination of Compressibility>

The compressibility was determined by a method comprising the steps of: storing low-substituted hydroxypropyl cellulose in a desiccator (relative humidity: about 11%) of 25° C. containing a saturated aqueous solution of lithium chloride for one week to control the water content to from 2.8 to 3.8% by weight; compressing the stored low-substituted hydroxypropyl cellulose into a 450 mg tablet at a tableting pressure of 10 kN (about 88.5 MPa) by using a table top type tablet press "HANDTAB 200" (product of ICHIHASHI SELKI) equipped with a round and flat punch having a diameter of 12 mm; and measuring the hardness of the tablet as the maximum strength at break when a load was applied to the tablet at a rate of 1 mm/sec in the tablet diameter direction by using a tablet hardness tester "TBH-125" (product of ERWEKA).

Example 2

Low-substituted hydroxypropyl cellulose was obtained in the same manner as in Example 1 except for the use of the sheet-like Pulp B derived from wood and having a length-weighted mean length of 2.76 mm and a length-weighted mean width of 28 μm. With regards to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Example 3

Low-substituted hydroxypropyl cellulose was obtained in the same manner as in Example 2 except that the amount of propylene oxide was changed to 8.0 parts by weight. With regard to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Example 4

Low-substituted hydroxypropyl cellulose was obtained in the same manner as in Example 2 except that the amount of propylene oxide was changed to 14.8 parts by weight. With regard to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Example 5

Low-substituted hydroxypropyl cellulose was obtained in the same manner as in Example 2 except that the amount of acetic acid placed in the kneader before the reaction product was dispersed was changed to 6.6 parts by weight (20% of the neutralization equivalent), the amount of acetic acid added after a portion of low-substituted hydroxypropyl cellulose was dissolved was changed to 26.4 parts by weight (80% of the neutralization equivalent), and a sieve having an opening of 150 µm was used for sifting after the pulverization. With regards to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Example 6

Low-substituted hydroxypropyl cellulose was obtained in the same manner as in Example 2 except that the amount of acetic acid placed in the kneader before the reaction product was dispersed was changed to 9.9 parts by weight (30% of the neutralization equivalent), an amount of acetic acid added after a portion of low-substituted hydroxypropyl cellulose was dissolved was changed to 23.1 parts by weight (70% of the neutralization equivalent), and a sieve having an opening of 150 µm was used for sifting after the pulverization. With regards to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Example 7

Low-substituted hydroxypropyl cellulose was obtained in the same manner as in Example 1 except for the use of the sheet-like Pulp C derived from wood and having a length-weighted mean length of 2.95 mm and a length-weighted mean width of 29 µm. With regards to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Comparative Example 1

Low-substituted hydroxypropyl cellulose was obtained in the same manner as in Example 1 except for the use of the sheet-like Pulp D derived from wood and having a length-weighted mean length of 2.33 mm and a length-weighted mean width of 26 µm. With regards to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Comparative Example 2

Low-substituted hydroxypropyl cellulose was obtained in the same manner as in Example 1 except for the use of the sheet-like Pulp E derived from wood and having a length-weighted mean length of 2.12 mm and a length-weighted mean width of 24 µm. With regards to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Comparative Example 3

Low-substituted hydroxypropyl cellulose was obtained in the same manner as in Example 1 except for the use of the sheet-like Pulp F derived from wood and having a length-weighted mean fiber length of 1.70 mm and a length-weighted mean width of 21 µm. With regards to the low-substituted hydroxypropyl cellulose thus obtained, the hydroxypropoxy content, average particle diameter, volume fractions of various particles (long and short fibrous particles, spherical particles, and fine particles), and compressibility were determined in the same manner as in Example 1. The results are shown in Table 1.

Tablets were produced using the low-substituted hydroxypropyl cellulose obtained above in each of Examples and Comparative Examples by the dry direct tableting as described below, and a capping incidence was determined.

(1) Preparation of Drug Granules to be Tableted

Acetaminophen powder (490 g, product of Yamamoto Chemical Ind.) was placed in a fluidized-bed granulator "Multiplex MP-01" (product of Powrec Corp.). It was granulated, while spraying thereto 200 g of a 5% by weight aqueous solution of hydroxypropylmethyl cellulose (hydroxypropoxy content: 8.8% by weight, methyl content: 29.0% by weight, and viscosity at 20° C. of a 2% by weight aqueous solution thereof: 3.0 mPa·s, product of Shin-Etsu Chemical Co., Ltd.) under the conditions of an intake air temperature of 60° C., an air flow rate of from 0.5 to 0.7 m³/min, an exhaust air temperature of from 30 to 35° C., a spray air pressure of 200 kPa, and a spray rate of 10 g/min. Then, after dried until the exhaust gas temperature reached 45° C., the dried granulated product was sifted through a sieve having an opening of 500 µm to obtain acetaminophen granules containing 98% by weight of acetaminophen.

(2) Tableting and Evaluation

After 90 parts by weight of the acetaminophen granules were mixed with 10 parts by weight of low-substituted hydroxypropyl cellulose, 0.5 parts by weight of magnesium stearate as a lubricant was added thereto and mixed. The resulting mixture was tableted using a rotary tableting machine "VIRGO" (product of KIKUSUI SEISAKUSHO) at a tableting pressure of 12.5 kN (about 249 MPa) and a tableting rate of 20 rpm to obtain each tablet having a diameter of 8 mm, a curvature radius of 12 mm, and a tablet weight of 200 mg. The capping incidence of the tablets thus obtained was determined. The results are shown in Table 1.

Fifty tablets were put in the drum of a friability tester TA (product of ERWEKA GmbH) and rotated 100 times at 25 rpm for 4 minutes. Then the number of tablets having capping caused, that is, the number of tablets cracked into two layers was counted and a capping incidence was calculated based on the following equation:

Capping incidence (%)={(The number of tablets having capping)/50}×100

TABLE 1

|  | length-weighted mean length of pulp (mm) | hydroxy-propoxy content (wt %) | average particle diameter (μm) | volume fraction of | | | | B/A | compressibility (N) | capping-incidence (%) |
|  |  |  |  | long fibrous particles A (%) | short fibrous particles B (%) | spherical particles (%) | fine particles (%) |  |  |  |
| --- | --- | --- | --- | --- | --- | --- | --- | --- | --- | --- |
| Example 1 | 2.56 | 11 | 58 | 20.6 | 26.3 | 49.2 | 3.9 | 1.27 | 162 | 0 |
| Example 2 | 2.76 | 11 | 61 | 25.8 | 31.9 | 39.2 | 3.1 | 1.24 | 189 | 0 |
| Example 3 | 2.76 | 8 | 63 | 27.1 | 33.1 | 36.5 | 3.3 | 1.22 | 195 | 0 |
| Example 4 | 2.76 | 14 | 59 | 24.6 | 30.6 | 41.8 | 3.0 | 1.24 | 182 | 0 |
| Example 5 | 2.76 | 11 | 63 | 37.5 | 33.0 | 27.1 | 2.4 | 0.88 | 194 | 0 |
| Example 6 | 2.76 | 11 | 64 | 45.2 | 33.9 | 19.1 | 1.8 | 0.75 | 199 | 0 |
| Example 7 | 2.95 | 11 | 65 | 31.9 | 36.3 | 29.1 | 2.7 | 1.14 | 218 | 0 |
| Comp. Ex. 1 | 2.33 | 11 | 45 | 13.5 | 21.8 | 60.4 | 4.3 | 1.61 | 136 | 6 |
| Comp. Ex. 2 | 2.12 | 11 | 52 | 7.6 | 17.4 | 70.1 | 4.9 | 2.29 | 114 | 12 |
| Comp. Ex. 3 | 1.70 | 11 | 54 | 2.6 | 11.0 | 80.7 | 5.7 | 4.23 | 96 | 22 |

The low-substituted hydroxypropyl cellulose being obtained in each of Examples 1, 2 and 7, and having a volume fraction of long fibrous particles of 15% or more, a volume fraction of short fibrous particles of 23% or more, and a degree of hydroxypropoxy substitution of 11%, was completely prevented from causing the capping. In addition, the more the length-weighted mean length of the pulp increased, the more the volume fractions of long and short fibrous particles increased, thereby showing the high compressibility. It is considered that improvement of the compressibility due to entanglement of fibrous particles could prevent the capping.

On the other hand, the low-substituted hydroxypropyl celluloses being obtained in each of Comparative Examples 1, 2 and 3, and having a volume fraction of long fibrous particles of less than 15%, a volume fraction of short fibrous particles of less than 23%, and a degree of hydroxypropoxy substitution of 11%, caused the capping. In addition, there is a tendency that the more the length-weighted mean length of pulp decreases, the more the volume fractions of long and short fibrous particles decrease, thereby deteriorating the compressibility and increasing the capping incidence.

Further, it is evident from the results of Examples 3 and 4 that irrespective of the degree of hydroxypropoxy substitution, the low-substituted hydroxypropyl cellulose having a volume fraction of long fibrous particles of 15% or more and a volume fraction of short fibrous particles of 23% or more can be completely prevented from capping. Comparing the low-substituted hydroxypropyl cellulose obtained in each of Examples 2, 3 and 4 in which each pulp had the same length-weighted mean length, as the degree of hydroxypropoxy substitution decreases, the volume fractions of long and short fibrous particles tend to slightly increase. This is considered to occur because as the degree of hydroxypropoxy substitution is lower, the low-substituted hydroxypropyl cellulose has more difficulty in dissolving in the precipitation step so that fibrous particles are apt to remain. However, the influence of the degree of hydroxypropoxy substitution on the volume fractions of long and short fibrous particles is restrictive compared with the influence of the length-weighted mean length of pulp on the volume fractions.

In Example 5 in which the amount of the acid placed before the reaction product was dispersed was 20% of the neutralization equivalent and in Example 6 in which the amount of the acid placed was 30% of the neutralization amount, an amount of the alkali necessary for dissolving the low-substituted hydroxypropyl cellulose is smaller than that in Example 2 in which the amount of the acid placed was 10% of the neutralization equivalent, so that long fibrous particles are apt to remain and a volume fraction of the long fibrous particles shows a large increase. On the other hand, a volume fraction of the short fibrous particles and compressibility in each of Examples 5 and 6 are slightly greater than those in Example 2, and their values are lower than the respective values in Example 7.

The invention claimed is:

1. Low-substituted hydroxypropyl cellulose having a hydroxypropoxy content of from 5 to 16% by weight, and having, on a basis of a dynamic image analysis to divide all particles into fine particles, spherical particles, and fibrous particles consisting of long and short fibrous particles, a volume fraction of the long fibrous particles relative to all of the particles of from 15 to 50% and a volume fraction of the short fibrous particles relative to all of the particles of from 23 to 60%,
wherein
the fine particles have a length of fiber of less than 40 μm,
the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a maximal Feret diameter to a minimal Feret diameter, of 0.5 or more, and a circularity, which is a ratio of a perimeter ($P_{EQPC}$) of a circle that has the same area as a projection area to a perimeter ($P_{real}$) of a real particle, of 0.7 or more,
the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7, and the short fibrous particles have a length of fiber of 40 μm or more and less than 200 μm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7.

2. The low-substituted hydroxypropyl cellulose according to claim 1, wherein the hydroxypropoxy content is in a range of from 11 to 16% by weight.

3. The low-substituted hydroxypropyl cellulose according to claim 1, which is produced from a pulp having a length-weighted mean length of from 2.40 to 3.50 mm.

4. A solid preparation, comprising the low-substituted hydroxypropyl cellulose of claim 1.

5. The solid preparation according to claim 4, wherein the solid preparation is a tablet.

6. The low-substituted hydroxypropyl cellulose according to claim 1, having a volume-based average particle size, determined by a dry laser diffractometry, of from 10 to 100 μm.

7. A solid preparation, comprising the low-substituted hydroxypropyl cellulose of claim 6.

8. A method for producing the low-substituted hydroxypropyl cellulose of claim 1 comprising the steps of:

bringing sheet-like pulp or chip-like pulp having a length-weighted average fiber length of from 2.40 to 3.50 mm into contact with an alkali metal hydroxide solution to obtain alkali cellulose;

reacting the alkali cellulose with propylene oxide to obtain a reaction product;

dispersing the reaction product in water comprising an acid to partially dissolve the reaction product therein, followed by neutralization with an acid to precipitate crude low-substituted hydroxypropyl cellulose;

washing the crude low-substituted hydroxypropyl cellulose to obtain washed low-substituted hydroxypropyl cellulose;

drying the washed low-substituted hydroxypropyl cellulose to obtain dried low-substituted hydroxypropyl cellulose; and pulverizing the dried low-substituted hydroxypropyl cellulose.

\* \* \* \* \*